United States Patent
Kashman et al.

(10) Patent No.: US 6,635,656 B1
(45) Date of Patent: Oct. 21, 2003

(54) CYTOTOXIC ALKALOIDS HALITULIN

(75) Inventors: Yoel Kashman, Tel-Aviv (IL); Ganit Koren-Goldshlager, Tel-Aviv (IL); Maria Dolores Garcia Gravalos, Tres Cantos (ES); Michael Schleyer, Durban (ZA)

(73) Assignee: Pharma Mar, S.A., Tres Cantos (ES)

( * ) Notice: Subject to any disclaimer, the term of this patent is extended or adjusted under 35 U.S.C. 154(b) by 0 days.

(21) Appl. No.: 09/807,083

(22) PCT Filed: Oct. 8, 1999

(86) PCT No.: PCT/GB99/03341

§ 371 (c)(1),
(2), (4) Date: Nov. 7, 2001

(87) PCT Pub. No.: WO00/20411

PCT Pub. Date: Apr. 13, 2000

(30) Foreign Application Priority Data

Oct. 8, 1998 (GB) .............................................. 9821975

(51) Int. Cl.$^7$ ............................................ C07D 401/14
(52) U.S. Cl. ...................................... 514/314; 540/481
(58) Field of Search ........................ 546/167; 540/481; 514/314

(56) References Cited

PUBLICATIONS

International Search Report; PCT/GB99/03341; J. Stellmach; Jan. 27, 2000.

"Polycitone A and Polycitrins A and B: New Alkaloids from the Marine Ascidian Polycitor sp."; A. Rudi et al.; J.Org.Chem; vol. 59, 1994; pp. 999–1003; XP002128245; Washington.

"Storniamides A–D: Alkaloids from a Patagonian Sponge Cliona sp"; J.A. Palermo et al; Tetrahedron, NL, Elsevier Science Publishers, Amsterdam; vol. 52, No. 8, 1996, pp 2727–2734; XP004104363; ISSN: 0040–4020.

"New Lamellarin Alkaloids from an Unidentified Ascidian from the Arabian Sea"; M.V.R. Reddy et al.; Tetrahedron, NL, Elsevier Science Publishers, Amsterdam; vol. 53, No. 10, 1997, pp. 3457–3466; XP004105426; ISSN: 0040–4020.

"Haliclorensin, a Novel Alkaloid from the Marine Sponge Haliclona tulearensis"; G. Koren–Goldshlager, et al.; J. Nat. Prod.; vol. 61, Feb. 1998; pp. 282–284; XP002128243 Columbus.

"Haliclonacyclamines A and B, Cytotoxic Alkaloids from the Tropical Marine Sponge Haliclona sp"; R.D. Charan et al; Tetrahedron, NL, Elsevier Science Publishers, Amsterdam; vol. 52, No. 27, Jul. 1996; pp. 9111–9120; XP004103999; ISSN: 0040–4020.

"The Haliclonacyclamines, Cytotoxic Tertiary Alkaloids from the Tropical Marine Sponge Halclona sp"; R.J. Clark et al.; Tetrahedron, NL, Elsevier Sciende Publishers, Amsterdam; vol. 54, No. 30; pp. 8811–8826; XP004124047; ISSN: 0040–4020.

"Halitulin, A New Cytotoxic Alkaloid from the Marine Sponge Haliclona tulearensis"; Y. Kashman et al.; Tetrahedron Letters, NL, Elsevier Science Publishers, Amsterdam; vol. 40, No. 5; Jan. 1999; pp. 997–1000; XP004151502; ISSN: 0040–4039.

"Total synthesis of cytotoxic sponge alkaloids Motuporamines A and B"; J.E. Baldwin et al.; Tetrahedron Letters, NL, Elsevier Science Publishers, Amsterdam; vol. 40, No. 29; Jul. 1999; pp. 5401–5404; XP004170105; ISSN: 0040–4039.

"A Concise Synthesis of Storniamide A Nonamethyl Ether"; H. Ebel et al; Tetrahedron Letters, NL, Elsevier Science Publishers, Amsterdam; vol. 39, No. 50, Dec. 1998; pp. 9165–9166; XP004142664; ISSN: 0040–4039.

"The Cytotoxicity and mode of action of 2,3,4–trisubstituted pyrroles and related derivatives in human Tmolt4 leukemia cells"; J.T. Gupton et al.; Pharmazie; vol. 54, No. 9; Sep. 1999; pp. 691–697; XP000872803; Berlin.

*Primary Examiner*—Bruck Kifle
(74) *Attorney, Agent, or Firm*—Fish & Richardson P.C.

(57) ABSTRACT

Compounds of general formula (I), wherein the nature of the group R is not particularly critical and typically takes various forms, include the natural compound halitulin of formula (I) and have antitumor activity.

2 Claims, No Drawings

CYTOTOXIC ALKALOIDS HALITULIN

The present invention relates to a new class of anti-tumor agents based on a new active compound isolated from a sponge.

BACKGROUND OF THE INVENTION

In connection with our long-standing interest in the chemistry and bioactivity of marine sponges, we found that extracts of the Indo-Pacific sponge *Haliclona tulearensis* (class Demospongiae, order Haplosclerida, family Chalinidae, genus Haliciona), collected in Sodwana Bay, Durban, South Africa, were quite cytotoxic. Many interesting N-containing metabolites came out from the genus Haliclona[1-6]. Recently, we reported the isolation of haliclorensin (1), a new N-(3'-arninopropyl)-3-methylazacyclodecane, from *H. tulearensis*[7] of the following formula (A):

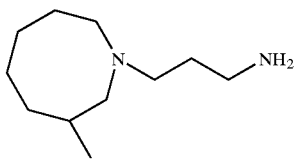

We have now discovered a new N-containing metabolite named halitulin with cytotoxic activity, which in turn has led us to a new class of active compounds.

SUMMARY OF THE INVENTION

According to the present invention, there is provided a compound of the general formula (I):

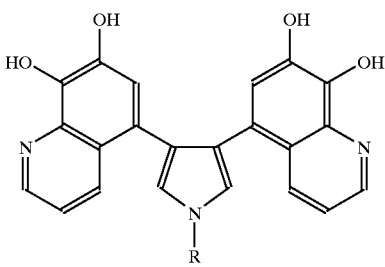

and related derivatives.

PREFERRED EMBODIMENTS

In particular, the present invention provides compounds of the given formula (I) wherein R is selected from:
a) a cycloamino-N-alkylene group of formula (II):

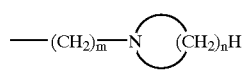

where m is typically 1 to 6, especially 3, and n is typically 3 to 20, especially 9, and which may be substituted on the ring, for example with one or more $C_1$–$C_6$ alkyl groups, especially with one methyl group β to the ring nitrogen;
b) a similar cycloaliphatic-alkylene group lacking the ring nitrogen;
c) an optionally substituted alkyl group, cycloalkyl group, aryl group, alkyl group or any other substituent group which does not undermine the activity of the compound, for example an aininoalkylene group of formula —$(CH_2)_p NR^1 R^2$, where p is typically 1 to 6, especially 3, and $R^1$ and $R^2$ are hydrogen, aryl or aralkyl;
d) hydrogen.

The nature of the group R is not critical.

Moreover, there can be one or more substituents on the quinoline rings, for example alkyl groups at one or more of the 2-, 3- and 4-positions of one or both quinoline rings.

The present invention further extends to related derivatives of the compounds of formula (I), which include:
a) derivatives of the phenolic hyrioxy groups, such as ethers or esters;
b) oxidised forms such as N-oxides and o-quinolinoquinones;
c) pharmaceutical acceptable acid addition salts In particular, we provide the compound halitulin of formula:

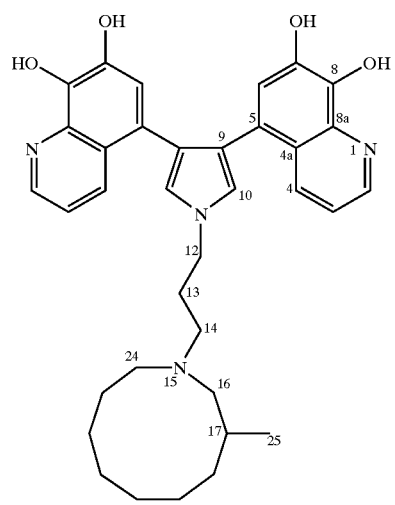

Halitulin, a substituted pyrrole, can be isolated from the sponge *Haticlona tulearensis*, and can be characterised by the following data:

$[\alpha]_D$+7.5°; (c=2.8, MeOH)

IR $\delta_{max}$ 3000–3400, 1623, 1597 cm$^{-1}$ $\lambda_{max}$(MeOH): 212 (29200), 252 (31600), 364 (4400);

and other data given later.

Over 250 pyrrole-containing compounds are known from marine organisms. A few that resemble the structure of halitulin are polycitone A, polycitrins A & B[8], the lamellarins[9] from ascidians and the storiamide[s10] and arcynibins[11] from sponges. Halitulin, to the best of our knowledge, is the first natural compound to be discovered that embodies a 7,8-dihydroxyquinoline system. A very few other dihydroxyquinoline-containing compounds are known e.g. luzopeptin, a terrestrial Actinomadura antimicrobial metabolite[20] and the marine sponge Verongia aerophoba metabolite 3,4-dihydroxyquinoline-2-carboxylic acid[21].

Halitutin (2) was found to have cytotoxic activity. The activity, $IC_{50}$ values, against cell cultures of P-388 murine leukemia, A-549 human lung carcinoma, HT-29 human colon carcinoma and MEL-28 human melanoma is 0.025, 0.012, 0.012 and 0.025 μg/ml respectively.

We know that the compound haliclorensin is inactive. From this knowledge, we can predict the activity in the compounds of the present invention.

The present invention also relates to pharmaceutical preparations which contain as active ingredient a compound of this invention, as well as processes for preparation. Methods of administration to patients are also envisaged.

Examples of pharmaceutical compositions include any solid (tablets, pills, capsules, granules, etc.) or liquid (solutions, suspensions or emulsions) with suitable composition of oral, topical or parental administration, and they may contain the pure compound or in combination with any carrier or other pharmacologically active compounds. These compositions may need to be sterile when administered parenterally, The correct dosage of a pharmaceutical composition comprising a compound of this invention will vary according to the pharmaceutical formulation, the mode of application, and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds may be provided in the pharmaceutical compositions of this intention in the form of a prodrug or precursor, which upon administration converts or is metabolised to the active compound.

The compositions of this invention may be used with other drugs to provide a combination therapy. The other drugs may form part of the same composition, or be provided as a separate composition for administration at the same time or a different time. The identity of the other drug is not particularly limited, and suitable candidates include:

- drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);
- antimetabolite drugs such as 5-fluorouracil, eytarabine, gemcitabine, purine analogues such as pentostatin, methotrexate);
- alkylating agents such as nutrogen mustards (such as cyclophospharnide or ifosphamide);
- drugs which target DNA such as the anitracycline drugs adriamycin, doxorubicin, phannorubicin or epirubicin;
- drugs which target topoisomerases such as etoposide;
- hormones and hormone agonists or antagonists such as estrogens, antiestrogens (tamoxifen and related compounds) and androgens, flutamide, leuprorelin, goserelin, cyprotrone or octreotide;
- drugs which target signal transduction in tumour cells including antibody derivatives such as herceptin;
- alkylating drugs such as platinum drugs (cisplatin, carboplatin, oxaliplatin, paraplatin) or nitrosoureas;
- drugs potentially affecting metastasis of tumours such as matrix metalloproteinase inhibitors;
- gene therapy and antisense agents;
- antibody therapeutics; and
- other bioactive compounds of marine origin, notably the ecteinascidins such as ET-743, or the didemnins such as aplidine.

EXAMPLES OF THE INVENTION

The present invention will be father illustrated with reference to the following examples which aid in the understanding of the present invention, but which are not to be construed as limitations thereof. All percentages reported herein, unless otherwise specified, are present by weight. All temperatures are expressed in degrees Celsius. All incubations are carried out at 28° C. and flasks are shaken in an orbital shaker at 250 rpm. All media and recipients are sterile and all culture processes aseptic.

IR spectra were recorded on a Nicolet 205 Ft-ir spectrophotometer. High resolution mass spectra ((HRMS) were obtained on a VG Fison autospec Q instrument. $^1$H and $^{13}$C-nmr were recorded on Bruker AMX-360 and ARX-500 spectrometers. All chemical shifts are reported with respect to TMS ($\delta_H$=0). Optical rotations were measured on a Perkin-Elmer Model 141 polarimeter using a 1-cm microcell.

*Haliclona tulearensis* was collected in Sodwana Bay, Durban, South Africa. A voucher sample of the organism (the sponge *Haliclona tulearensis*) from which hialitulin (2) has been isolated, has been deposited at the Oceanographic Research institute in Durban, South Africa, having the Deposit Number TASA-121 and having been deposited in July 1992.

Freshly collected *H. tulearensis* was frozen on site and kept frozen until needed. Freeze-dried sponge tissue (32 g, dry wt) was extracted with methanol-EtOAc (1:1) to give a brown guni (2.9 g) after evaporation. The two latter fractions were individually fractionated by repeated chromatography on Sephadex LH-20 (eluting with $CHCl_3$:MeOH, 1:1) to afford halitulin (2, 180 mg, 0.56% dry wt)[12]

Halitulin (2) was analyzed for $C_{35}H_{40}N_4O_4$ by HREIMS (m/z 580.3054, 100% Δmmu−0.5) confirmed by positive and negative FABMS (m/z 581 and 579, respectively). The $^{13}$C NMR spectrum (Table 1) showed, however, only 24 resonances-thirteen sp3 carbons (one methyl, eleven methylenes and one rnethine) and eleven $sp^2$ carbons (five methine and six quaternary carbons) implying, therefore, the duplication of eleven carbon atoms. The duplicated part, according to the integration of the proton signals, was determined to be the aromatic portion of the molecule. Comparing the NMR data of the aliphatic part of 2 (Table 1) with haliclorensin (1)[7], together with the COSY, TOCSY, and HMBC data, established their identity. The incorporation of 1 in halitulin was further supported by the two MS fragments at m/z 168 ($C_{11}H_{22}N_+$, 48%) and m/z/399 (MW$^+$-$C_{12}H_{24}N$, 90%), resulting from the preferable αβ to the aliphatic nitrogen-atoms[1] fragmentation at C-13,14 and C-12,13 respectively. Determination of the haliclorensin moiety in 2 left $C_{22}H_{14}N_3O_4$ (including the adjoining N-atom) with 17 degrees of unsaturation to be accounted for. Strong absorptions centred at 3200 cm$^{-1}$ in the IR spectrum, the presence of four oxygen atoms in 2 and the absence of carbonyls and ethereal C-atoms in the $^{13}$C NMR spectrum suggested four OH groups. Indeed, acetylation of 2, with a 1:1 mixture of $Ac_2O$/pyridine, overnight at room temperature., afforded a very unstable tetra phenol acetate (3), on the basis of the HREIMS which gave the suitable molecular ion and also four subsequential losses of 42 mass units, and no loss of 60 mass units[13]. The four phenol acetate groups were in full agreement with the 1773 cm$^{-1}$ IR absorption and the new methyls in the proton NMR. Furthermore, the $^1$H-NMR spectrum, showing only two new signals at δ 2.37 and 2.50 ppm integrating for 6H each (in comparison with $H_3$-25), pointed clearly to symmetry in the aromatic part of 2. The eleven $sp^2$ C-atoms, suggested six different double bonds, of which at least one has to be a C=N bond. A priori more than one structure is possible, however, accounting for the above data, especially the 1D and 2D NMR spectra (Table 1), only one structure (discussed below)

is possible, namely a diquinolinylpyrrole. Two of the double bonds, carrying H-2 ($\delta$ 8.56) and H-10 ($\delta$ 7.04), with $^1J_{CH}$ values of 179 and 184 Hz, respectively, have to be adjacent to N-atoms, and moreover to be pan of quinoline and pyrrole[14]. The $^1$H and $^{13}$C chemical shifts of the aromatic pat (Table 1) implied a substituted quinoline system. Furthermore, the three proton spin system, confirmed by a COSY experiment [$\delta$ 8.56 d($J_{2,3}$=4.9 Hz), 7.20 dd (J=8.3 Hz) and 8.51 d($J_{3,4}$=8.3 Hz) indicated, according to the 4.9 Hz coupling characteristic for a coupling constant next to a nitrogen atom, that the pyridine ring of the system is free of substitution. On the other hand, the adjacent benzene ring, carrying a single proton ($\delta$ 7.28 brs) has to be three substituted. That is, one position being the linkage to the rest of the molecule and two others bear OH groups. Empirical calculations of the carbon chemical shifts[15] agreed best with a 5-substituted-7,8-dihydroxyquinoline, a suggestion that was confirmed in two ways: a reaction of halitulin with NaIO$_4$ (known to oxidize catechols to oquinones)[16] in a 1:1 mixture of EtOH:H$_2$O, afforded, on the basis of the change in the UV spectrum[17] and change in color from orange to red, an o-quinorie and b, from the measured NOE's vide infra. All the above data suggested a 3,4-diquiolioiylpyrrole, which is in fill agreement with the results from the HMBC experiment. To distinguish between very close shifts of C-4a, 6 and 10, a 1D INAPT experiment was undertaken[18]. Two key NOE's that supported unequivocally the suggested structure, were between H-6 and H-10 and between H4 and H —10. Both NOE's being possible due to rotation around the C-5,9 bond, and only possible for the suggested isomer.

Compound 2 is sensitive to light and air, conditions under which, most likely, acyclodecane-nitrogen oxidizes. This is seen from the appearance of a weak peak at m/z M+16 in the mass spectrum. As a result, two N-oxide isomers are obtained causing the appearance of two new double methyl resonances (Me-25) in the NMR spectrum. Subsequently, the dihydroxy quinoline also oxidizes to the o-quinolinoquinone.

The structure of halitulin, as far as the aromatic part is concerned, resembles the polycitone[1] and the lamellarins[2]. However, the two phenyl-C$_3$ units of the latter's biogenthic precursors, are suggested in this case, to be replaced by two 5-substituted-quinoline-C$_3$ compounds, the biogenesis of which is not simple. The haliclorensin (1) biogenesis (replacing the phenethyl amine, as suggested earlier, for the above compounds[7]) is similar to the one suggested for manzamine C[22].

TABLE 1

$^1$H(500 MHz) and $^{13}$C(125 MHz) NMR data of halitulin (2) in CDCl$_3$.

| No. | $\delta_c$(m) | $\delta_H$(m, J in Hz) | HMBC (H to C) |
|---|---|---|---|
| 2 | 145.1 d | 8.56 (d, 4, 9) | 3, 4, 8a |
| 3 | 117.1 d | 7.20 (dd, 8.3, 4.9) | 2, 4a |
| 4 | 141.6 d | 8.51 (d, 8.3) | 2, 5, 8a |
| 4a | 122.9 | | |
| 5 | 126.7 s | | |
| 6 | 123.2 d | 7.28 brs | 4a, 7, 8, 9 |
| 7 | 148.1 s | | |
| 8 | 131.2 s | | |
| 8a | 130.1 s | | |
| 9 | 118.8 s | | |
| 10 | 122.6 d | 7.04 brs | 5, 9, 12 |
| 12 | 46.8 t | 4.23 (t, 6.3) | 10, 13, 14 |
| 13 | 26.1 t | 2.56 (m) | |
| 14 | 54.4 t | 3.23 (m) | |
| 16 | 57.7 t | 3.27 (m), 2.97 (m) | |
| 17 | 28.3 | 2.32 (m) | |
| 18 | 32.7 t | 1.60 (m) | |
| 19 | 24.4 t | 1.36–1.62 (m) | |
| 20 | 24.2 t | 1.36–1.62 (m) | |
| 21 | 23.9 t | 1.36–1.62 | |
| 22 | 23.6 | 1.36–1.62 (m) | |
| 23 | 22.0 t | 1.96 (m) | |
| 24 | 50.9 t | 3.40 (m), 3.75 (m) | |
| 25 | 20.07 q | 1.09 (brs) | |

[a]exchangeable. [b]The chemical shifts are strongly influenced by concentration and pH e.g. C-4a, 6 and 10 resonated in another experiment at 122.5, 122.5 and 122.1 respectively. [c]The following $^1J_{CH}$- values have been measured for C-2,3, 4,6 and 10: 179, 166, 161, 160 and 184 Hz respectively. [d] Besides the COSY correlations of H-2-4, the aliphatic protons gave the expected COSY, TOCSY and HMSC correlations as detailed for haliclorensin earlier[7].[e] INAPT correlations were found between (H to C): 2/8a, 3/4a, 4/5,8a 6/4a,8,9 and 10/9.

References and Notes

1. Chara, R. D.; Garson, M. J.; Breretozi, I. M.; Willis, A. C.; Hopper, J. N. A. *Tetrahedron*, 1996, 52, 9111–9120.
2. Baker, B. J.; Scheuer, P. J.; Shoolery, J. N. *J Am. Chem, Soc*, 1988, 110,965–966.
3. Fahy, E.; Molinski, T. F.; Harper, M. K.; Sullivan, B. W.; Faulkner, D. J. *Tetrahedron*, 1988, 29,3427–3428
4. Fusetarii, N.; Yasumoto, K.; Matsunaga, S. *Tetrahedron Lett*, 1989, 30, 6891–6894.
5. Sakai, R; Kohmoto, S; Higa, T. *Tetrahedron Lett*. 1987, 28, 5493–5496.
6. Sakai, R; Higa, T; Jefford, C. W.; Bernardinelli, G. J. *Am. Chem. Soc*, 1986, 108, 6404–6405.
7. Koren-Goldstilager, G; Kashman, Y; Sclileyer, M *J Nat. Prod.*, 1988 61,282–289.
8. Rudi, A; Goldberg, I; Stein, Z. Frolow, F; Benayahu, Y; Schleyer, M; Kashmn, Y. *J. Org. Chem.*, 1994, 55,999–1003.
9 Venkata, M; Reddy, R; Faulkner, D. J. *Teirahedron*, 1997, 53, 3457–3466.
10. Palermo, J. A.; Brasco, M. F. R.; Seldes, A. M. *Tetrahedron*, 1996, 52, 2727–2434.
11. Steglich, W; Steffan, B; Kopaiski, L; Eckhardt, G., *Agnew. Chem* (Int. Ed) 1980, 19, 459–460.
12. 2, orange foaming oil; [α]$_D$+7.5 (c 2.8, MeOH), $\upsilon_{max}$3000–3400, 1623, 1597 cm$^{31}$ $^1$, $\lambda_{max}$ (MeOH) 212 (29200), 252(31600), 364(4400$\lambda_{max}$(MeOH+OH) 214 (24700), 264(14800), 350(4650).
13. 3: EIMS m/z (748(5%), 706(50), 664(100), 622(100), 580(48), 525(10), 483(25), 441(42), 399(98), 168(37), HREI 664.3261(Δmmu 1.1), 399,1220(Δmmu –0.1). $\delta_H$(J in Hz) 0.9.0 (d, 3H, J=6).1.51 (brs, SH), 1.61–1.69 (m. 10H), 1.86 (m, 1H), 1.97 (mi, 1H) 2.22(m, 1H), 2.24 (m, 1H), 2.37 (brs, 6H), 2.50 (brs, 6H), 2.65 (m, 1H), 2.84 (brt, 1H), 4.16 (m, 2H), 7.03 (brs, 2H), 7.15 (dd, 2H, J=8,4), 7.28 (brs, 2H), 8.23 (d, 2H, J=8.6), 8.76 (d, 2H, J=2); $\delta_c$ 19.59, 20.6 qx2, 20.7 qx2, 22.3 t, 24.5 t, 24.7 t, 26.0 t, 26.5 t, 29.0 t, 30.2 t, 31.9 t, 48.5 t, 52.3 t, 53.5 t, 60.8 t, 120.6 s, 120.7 d, 121.7 d, 123.4 d, 125.9 s, 132.4 s, 134.6 d, 14.7 s, 142.1 s, 150.5 d, 168.1 s, 168.5.
14. Pretsch, E; Seibl, J; Clerc, T; Simon, W. *Tables of Spectral Data for Structure Determination of Organic Compounds*, Springer-Verlag, Berlin 1983.

15. Spec Tool, version 1.0, Chemical Concepts Gub H.
16. Takata, T; Tajima, R; Anda W. *J. Org. Chem.*, 1983, 48, 4764–4767.
17. 2-o-quinone; $\lambda_{max}$ (MeOH) 219 (12700), 248 (7400), 348 (3300), 457 (800) - see reference 14.
18. Drawn, S; Kanilowski, H. O.; Berger, S. 100 *and More Basic NMR Experiments*, VCH, 1996 p203.
19. Because of the symmetry of 2, the discussion regarding the one half is, or course, also valid for the identical second half.
20. Wakelin, L. P. G. *Med. Res. Revs.*, 1986, 6,275–339.
21. Fatorusso, E.; Forenza, S.; Minole, L.; Sodano, G. *Gazz. Chem. Ital*, 1971, 101, 104–107.
22. Tsuda, M; Kawasaki, N; Kobayashi J. *Teirahedron Lett*, 1994, 35, 4387–4388.

Biological Activity

The compound of the present invention, Halitulin (2) exhibits antituixnor activity against cell line derived from human tumors, such as P-388 mouse lyniphoma, A-549 human lung carcinoima, HT-29 human colon carcinoma and MEL-28 human melanoma. Also provides a method of treating any mammal affected by a malignant tumor sensitive to Halitulin (2) which comprises administering to the affected individual a therapeutically effective amount of Halitulin (2) or a pharmaceutical composition thereof.

Cell Cultures. Cells were maintained in logarithmic phase of growth in eagle's Minimum Essential Medium, with Earle's Balanced Salts, with 2.0 nmm L-glutamine, with non-essential amino acids, without sodium bicarbonate (EMEM/neaa); supplemented with 10% Fetal Calf Serum (FCS), $10^{-2}$ M sodium bicarbonate and 0,1 g/l penicillin-G+streptomycin sulfate.

A simple screening procedure has been carried out to determine and compare the antitumor activity of these compounds, using an adapted form of the method described by Bergeron et al. (1984)(1). The antitumor cells employed have been P-388 (suspension culture of a lymphoid neoplasm from DBA/2 mouse), A0549 (monolayer culture of a human lung carcinoma), HT-29 (monolayer culture of a human colon carcinoma) and MEL-28 (monolayer culture of a human melanoma).

P-388 cells were seeded into 16 mm wells at $1\times10^4$ cells per well in 1 ml aliquots of MEM 5FCS containing the indicated concentration of drug. A separate set of cultures without drug was seeded as control growth to ensure that cells remained in exponential phase of growth. All a 98% humid atmosphere, an approximately IC50 was determined by comparing the growth in wells with drug to the growth in wells control.

A-549, HT-29 and MEL-28 cells were seeded into 16 mm wells at $2\times10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately IC50 was determined by comparing the growth in wells with drug to the growth in wells control.

1. Raymond J. Gergeron, Paul F. Cavanaugh, Jr., Steven J. Kline, Robert G. Hughes, Jr., Gary T. Elliot and Carl W. Porter. antineoplastic and antiherpetic activity of spermidine catecholamnide iron chelators. *Biochem. Bioph. Res. Comm.* 1984 121(3), 848–854.
2. Alan C. Schiroeder, Roben G. Hughes, Jr. and Alexander Bloch. Effects of Acyclic Pyrimidine Nucleoside Analogues. *J. Med. Chem*1981, 24 1078–1083.

| | IC50 ($\mu$g/ml) | | | |
|---|---|---|---|---|
| Compound | P-388 | A-549 | HT-29 | MEL-28 |
| Halitulin | 0.025 | 0.0125 | 0.0125 | 0.025 |

What is claimed is:
1. A halitulin compound of formula

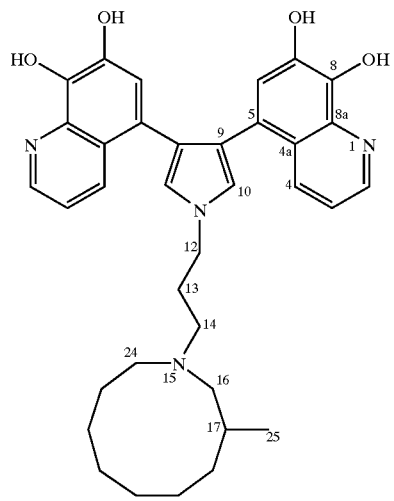

or a pharmaceutically acceptable acid addition salt thereof.

2. A method of preparation of halitulin, which comprises:
  (a) extraction of compounds from tissue of the sponge *Haliclona tulearensis* using a suitable solvent, and
  (b) separation of halitulin from the extracted compounds by chromatography.

* * * * *